United States Patent [19]
Goodheart et al.

[11] Patent Number: 5,750,378
[45] Date of Patent: May 12, 1998

[54] METHOD FOR PREPARING CELLULAR FIBRONECTIN

[75] Inventors: Clyde R. Goodheart, Lincolnshire; Ralph H. Silverman, Morton Grove, both of Ill.

[73] Assignee: Fibrogenex, Inc., Chicago, Ill.

[21] Appl. No.: 779,383

[22] Filed: Jan. 7, 1997

Related U.S. Application Data

[63] Continuation-in-part of Ser. No. 302,180, Sep. 8, 1994, abandoned, which is a continuation-in-part of Ser. No. 811,269, Dec. 20, 1991, Pat. No. 5,354,269.

[51] Int. Cl.$^6$ ........................................ C12N 5/00
[52] U.S. Cl. ..................... 435/70.3; 435/70.1; 435/41; 435/404; 435/405
[58] Field of Search ........................... 435/70.3, 70.1, 435/41, 404, 405

[56] References Cited

U.S. PATENT DOCUMENTS

| | | |
|---|---|---|
| 5,128,321 | 7/1992 | Murray et al. . |
| 5,262,403 | 11/1993 | Nicolson et al. . |
| 5,270,300 | 12/1993 | Hunziker . |
| 5,354,269 | 10/1994 | Goodheart et al. . |

*Primary Examiner*—Leon B. Lankford, Jr.
*Attorney, Agent, or Firm*—Clark & Elbing LLP

[57] ABSTRACT

A method for producing cellular fibronectin, said method comprising incubating fibronectin-producing cells in a fibronectin production medium comprising: (a) 1.0–3.5 g/L bicarbonate salt; (b) 1.0–5.0 g/L glucose; (c) 10–30 µg/L dexamethasone; (d) 1–10 g/L hydrolyzed protein; and (e) 5–15 µg/L insulin.

5 Claims, No Drawings

METHOD FOR PREPARING CELLULAR FIBRONECTIN

This application is a continuation-in-part of U.S. application Ser. No. 08/302,180, filed Sep. 8, 1994, now abandoned which in turn is a continuation-in-part of U.S. application Ser. No. 07/811,269, filed Dec. 20, 1991 now U.S. Pat. No. 5,354,269.

FIELD OF THE INVENTION

This invention relates to a method for preparing fibronectin and more particularly, this invention relates to a method for preparing cellular fibronectin.

BACKGROUND OF THE INVENTION

U.S. Pat. No. 4,728,637 (Silverman) discloses a pharmaceutical protein complex which includes fibronectin for treating humans and animals with degenerative diseases. The complex disclosed in Pat. No. 4,728,637 or, alternatively, a pure fibronectin composition, is used in the treatment of cancer resections as described in parent application 07/811,269.

The aforementioned fibronectin which is produced by the inventive process herein comprises macromolecules produced from human and animal cultured cells, i.e. mesenchymal cells. As discussed in U.S. Pat. No. 4,728,637, fibronectin and procollagen are part of the compositions of that patent. Whether or not proteoglycan, laminin or elastin are present in the patent composition depends on the particular mesenchymal cell culture used to prepare the complex of the patent.

For purposes of simplification, the above composition of Pat. No. 4,728,637 is referred to as PROFIPEL. It is to be understood that this covers those instances where the composition contains all five ingredients—fibronectins, procollagens, proteoglycans, laminins and elastins; four ingredients—fibronectins, procollagens, proteoglycans, and either elastins or laminins; three ingredients—fibronectins, procollagens and proteoglycans, or the two ingredients, fibronectins and precollagens.

The cellular fibronectin produced by the present process has as one of its uses the treatment of cancer resections.

Postoperative recurrence of cancer locally in the incision site is a major problem with the surgical treatment of cancer. Local recurrence predominantly occurs in the central scar and under the skin graft. For instance, chest wall recurrence after radical mastectomy for breast cancer occurs in 10 to 15% of the patients (*Cancer* 20:1051–1053, 1967; *Cancer* 57:1421–1425, 1986; *J. Surg Oncol* 30:149–151, 1985; *Arch Surg* 111:323–325, 1976). The prognostic significance of local recurrence is ominous, with 3.9% and 0% survival after 5 and 10 years, respectively (*Cancer* 20:1051–1053, 1967). Depending on the site and type of cancer, local recurrences occur in 5% to 60% of patients undergoing surgical treatment for other kinds of cancer. Research scientists have formulated the hypothesis that such recurrences are due to facilitated lodgement, and subsequent growth, of cancer cells from the patients' circulation at the surgical wound area (*Cancer* 20:23–30, 1967; *J Surg Oncol* 30:33–45, 1985; *Ann Surg* 168:887–890, 1968; *Cancer Res* 12:929–932, 1959; *Cancer* 28:545–552, 1971). Local recurrence may also result from inadequate removal of the cancer, i.e., due to leaving cancer cells in the operative site. Similar problems occur in veterinary medicine. In veterinary surgical treatment of animals for cancer, local recurrences may occur for the same reasons as in humans.

SUMMARY OF THE INVENTION

Accordingly, it is an object of the present invention to provide a novel process for preparing cellular fibronectin.

It is another object of the present invention to provide a method of preparing cellular fibronectin comprising the steps of preparing cells from tissue; suspending said cells in a tissue culture medium; incubating the suspended cells to produce a confluent cell culture containing the tissue culture medium; replacing the tissue culture medium with a fibronectin production medium; harvesting the fibronectin production medium from the incubated cells to provide harvested fibronectin production medium; purifying the harvested fibronectin production medium to provide purified fibronectin production medium; recovering substantially pure fibronectin from the purified fibronectin production medium.

The objectives and advantages of the present invention are achieved, in a preferred embodiment by providing a method of preparing fibronectin. Minced tissue is added to a trypsin solution to dissociate cells. The trypsin solution is centrifuged to provide tissue cells. The tissue cells are suspended in a fibroblast culture medium and fetal bovine serum. This is incubated to form a monolayer of cells. The monolayer of cells is removed from the container by rinsing the cells with a solution of ethylenediamine tetraacetic acid. The rinsed cells are treated with fresh trypsin solution. The trypsin-treated cells are transferred to a second container containing a second culture medium which is the same as the first tissue culture medium. The cells are allowed to grow and then the second tissue culture medium is replaced with a fibronectin production medium. The fibronectin production medium is harvested from said cells and replaced with fresh fibronectin production medium. The harvested production medium is purified by filtering the harvested production medium to remove cells or cell debris. The purified production medium is generally exposed to an affinity chromatography column for eluting fibronectin from the column. Urea is removed from the fibronectin and the urea-less eluted fibronectin is collected and lyophilized.

DETAILED DESCRIPTION OF THE INVENTION

The present invention provides fibronectin by generally using human or animal tissue—the mesenchymal tissue. The mesenchymal cells were recovered from the mesenchymal tissue in a known manner. After being in tissue culture medium containing an antibiotic, the tissue was removed, minced and mixed with an appropriate solution such as a trypsin solution having 0.25% of trypsin 1:250 in phosphate buffered saline containing 0.02% EDTA (ethylenediamine tetraacetic acid) and no calcium or magnesium salts. The minced tissue remained in the trypsin solution at room temperature for about 15 to about 60 minutes and preferably for about 45 minutes. The preferred cells are collected generally by gentle centrifugation, and are then resuspended in a tissue culture medium which is preferably a fibroblast culture medium supplemented with a cell producing aid such as fetal bovine serum. We use as our fibroblast culture medium either MCDB 105 OR MCDB 202. These are well known fibroblast culture mediums and are defined, as follows: for MCDB-105, Sigma cell culture catalogue No. M-6395; and for MCDB-102, W. L. McKeehan & R. G. Ham, pages 100 and 101. Other fibroblast culture mediums may be utilized. We add about 10% fetal bovine serum to MCDB 202 and about 5% fetal bovine serum to MCDB 105. The resuspended cells were incubated for about 1 to about 10 days. The tissue culture medium was changed after about a week's incubation with the same or similar fresh fibroblast culture medium containing the cell producing aid. The cells form a complete monolayer after about ten days' incubation. The cells are removed from the surface of the culture vessel by rinsing first with EDTA solution and then treating with a trypsin solution. The cells were split in a ration of 2:1 to 5:1 and mixed with the same tissue culture growth medium described above. In five more days of incubation, the cells were split in a similar ratio once again and mixed with the same growth medium as before.

After the cells had again formed a confluent sheet, the growth medium was replaced with a fibronectin production medium that causes the cells to produce protein while minimizing cell growth. An economical fibronectin production medium is a fibroblast production medium such as standard Medium 199, for Medium 199, JRH BIOSCIENCES, Catalog No. 56-319; obtained from a commercial source as a dry powder and reconstituted with tissue culture grade distilled water according to manufacturer's instructions. Any appropriate fibroblast production medium may be used. To prepare the fibronectin production medium, the following ingredients were added to the Medium 199:

1. a source of amino acids i.e. various amino acids, essential and non-essential amino acids, lactalbumin hydrolysate and mixtures thereof;

2. a buffer to maintain the pH within the range of about 7 to 7.8 and preferably at about 7.4, i.e., sodium bicarbonate;

3. another buffer to also maintain the pH within the range noted above. The preferred buffer is a mixture of acid and sodium salt of HEPES (N-2-hydroxyethyl-piperazine-N'-(2ethanesulfonic acid);

4. an antibiotic such as penicillin and/or streptomycin;

5. protein producing aids such as a mixture of glucose, insulin and dexamethasone.

The substantially pure fibronectin we prepare and use is shown in the following examples which are:

EXAMPLE 1

Foreskins were obtained from newborns circumcised in a hospital nursery. The foreskins were transported to the laboratory in a culture medium containing penicillin and streptomycin at a concentration of 10,000 units/mL and 10 mg/ml, respectively. Each foreskin was minced with sterile scissors into pieces less than 1 mm in diameter, and stirred in trypsin solution (0.25% of trypsin 1:250 in phosphate buffered saline containing 0.02% EDTA (ethylenediamine tetraacetic acid and no calcium or magnesium salts) at room temperature for 45 minutes to dissociate the cells. The cells were collected by gentle centrifugation and resuspended in 20 ml of MCDB 202 fibroblast culture medium supplemented with fetal bovine serum (10%). The resuspended cells were then placed in 4 60×15 mm style tissue culture petri dishes. The cultures were incubated at 36° in a humidified incubator flushed with 5% $CO_2$ in air. The medium was changed after a week's incubation, and the cells had formed a complete monolayer after ten days' incubation. However, it is possible to incubate the cells for a much shorter time period, e.g. for one day. The cells were removed from the surface of the culture vessel by rinsing first with EDTA solution (described above) and then treating with the trypsin solution described above. The cells were transferred to plastic roller bottles (In Vitro Scientific Products, Inc., Ventura, Calif., 2× Bottle, area 1780 cm²), at a split ratio of 4:1 based on relative surface areas, using 100 ml/bottle of the same growth medium described above. In five more days of incubation, the cells had completely covered the surface of the roller bottle, and were split once more as before.

After the cells had again formed a confluent sheet, the medium was replaced with fibronectin production medium (100 ml/bottle). This medium was standard Medium 199, obtained from a commercial source as a dry powder and reconstituted with tissue culture grade distilled water according to manufacturer's instructions. The following ingredients were added to the standard Medium 199: lactalbumin hydrolysate 5 g/l; sodium bicarbonate, 2.2 g/l; HEPES buffer, free acid, 0.794 g/l; HEPES buffer, sodium salt, 1.735 g/l; penicillin 100,000 units/l; streptomycin 0.1 g/l; glucose 3 g/l; insulin 10 mg/l; dexamethasone 20 µ/l; solution containing essential amino acids, obtained commercially from Sigma Chemical Co., St. Louis, catalog #M7020, 20 ml/l; solution containing nonessential amino acids, obtained commercially from Sigma Chemical Co., catalog #M7145, 10 ml/l. Variations on the medium are contemplated.

Thus, we have discovered that optimal, high-level cellular fibronectin production can be achieved in tissue culture in which the tissue culture medium is fortified with a number of components, as follows: (a) 1.0 to 3.5 g/L bicarbonate salt; (b) 1.0–5.0 g/L glucose; (c) 10–30 mg/L dexamethasone; (d) 1–10 g/L hydrolyzed protein; and (e) 5–15 mg/L insulin. In preferred embodiments, the high-fibronectin production medium of the invention further contains an antibiotic, e.g., 50,000–200,00 units/L penicillin or 0.05 to 0.2 g/L streptomycin, and also contains 5–25 mmol/L HEPES buffer, to give a pH of 6.8 to 7.9.

The fibronectin production medium was left on the cells for a time sufficient to eliminate fetal bovine serum remaining from the growth medium, i.e., 2 hours to about 2 days. The fibronectin production medium was then discarded and replaced with fresh fibronectin production medium. This medium was harvested from the cells every two to four days and replaced with fresh production medium.

Because of the well known susceptibility of cellular fibronectin to degradation by proteases, the fibronectin was purified from each batch of medium harvested from the cells as soon as possible on the same day it was harvested, using the following procedure that permitted purification in minimum time. The medium was filtered through a fiberglass filter to remove any cells or cell debris that might be present. The harvest was pumped through an affinity chromatography column containing a bed of gelatin-agarose. Except for a small sample for testing, the medium was discarded after passing through the column. The column bed was flushed with an equilibration buffer—(sodium phosphate 10 mM, sodium chloride 150 mM, pH 7.2) until the absorption at 280 nm had returned to baseline. Elution buffer (Tris basic 50 mM, urea 4M, pH 7.5) was pumped through the column to elute the fibronectin from the affinity bed. A single sharp absorptive peak was collected. The fractions containing the peak were pooled and passed through a G-25 column equilibrated with water to remove the urea. A broad peak was collected containing protein. This was filtered through a sterile 0.2 µm filter for sterilization after adding 3.6 ml of concentrated phosphate buffer, so that after lyophilization (freeze drying), the reconstituted freeze-dried product would contain fibronectin, phosphate buffer, pH 7.5, and NaCl. It was then dispensed aseptically into sterile vials to contain 1 mg each of fibronectin composition.

Samples taken during the procedure and after lyophilization were analyzed on PAGE-SDS under reducing conditions. The patterns of bands on the gels indicated that the product was cellular fibronectin with a high degree of purity.

EXAMPLE 2

The process for preparing mouse cellular fibronectin was essentially the same as that described above in Example 1 for human cellular fibronectin. Mouse embryos were obtained from Strain A mice in about the 16th day of gestation, when they were about 1.2 cm long. They were removed from the uterus and membranes, decapitated, eviscerated, and minced into pieces smaller than 1 mm diameter. The tissue was trypsinized as described above for human newborn foreskins. After centrifugation, the cells from five embryos were dispensed into two plastic roller bottles in medium MCDE 202 supplemented with 10% fetal bovine serum. After a week of growth, the cells were transferred to eight new bottles using the same medium.

After the cells became confluent, the medium was changed to the fibronectin production medium used in Example 1. The first harvest was discarded after two days. Every two days after that, mouse cellular fibronectin was purified from the medium as described in Example 1. In one such harvest of 700 ml, the fibronectin eluted from the affinity column in fractions 7, 8 and 9. This was desalted by passing through a G-25 column, with the peak in fractions 9, 10, and 11. After sterilization, the final yield was 7.28 mg. Analysis on PAGE-SDS under reducing conditions revealed a tight cluster of bands at the same position as the human cellular fibronectin and at a slightly higher molecular weight position than the commercial bovine plasma fibronectin used as a marker.

EXAMPLE 3

A wedge of liver is surgically resected in a group of Strain A mice by electrocautery. Subsequently, 100,000 of the TA3Ha continuous line of experimental tumor cells were injected into the tail vein. Prior to injection, the cells had been treated by mixing them with solutions of various concentrations of bovine plasma fibronectin purchased from commercial sources or human or mouse cellular fibronectins prepared according to Examples 1 and 2 and allowing them to stand for one hour at room temperature. The results are shown in Table 1.

TABLE I

Number of animals with tumors at 14 days

| Treatment | n | Lung | P | Surgical Liver | P |
|---|---|---|---|---|---|
| Control | 240 | 129 (54%) | | 107 (45%) | |
| Bovine pFN | 34 | 8 (24%) | NS | 5 (15%) | NS |
| Human cFN | 48 | 17 (35%) | NS | 11 (23%) | NS |
| Mouse cFN | 73 | 15 (21%) | NS | 7 (10%) | <.005 |

(a) Surgical liver = that part of the liver that was operated upon
(b) pFN = plasma fibronectin
(c) cFN = cellular fibronectin
(d) NS = not significant; chi-square test used throughout These results show that fibronectin from bovine plasma decreased the percentage of animals with implants in either the lungs or the liver. Both the cellular fibronectin from a different species (human) and from the same species (mouse) reduced the incidence of metastatic implants, but the same-species material did so about twice as effectively as the cross-species material. In the experiments in Table 1, the incidence of metastatic implants in the surgically injured liver treated with mouse cellular fibronectin dropped from 45% to 10% as a result of the treatment, and the difference was statistically significant. A similar decrease of implants occurred in the lungs, which is the only organ that develops a significant number of tumors in unoperated animals when the cells are injected in the tail vein. In this instance, the action of the fibronectin was on the cells, since they were exposed to the fibronectin prior to being injected.

EXAMPLE 4

In this example, the surgically exposed tissue surface is treated by topically applying the fibronectin or PROFIPEL to the exposed tissue surface. This treatment is exemplified in Example 4, wherein Strain A mice were first operated upon by making a wedge resection of the liver by electrocautery, as in Example 3. The cut surface of the liver was treated topically by painting the cauterized surface with a solution of 1.0 mg of fibronectin in 1 ml of Ora-Plus gel (purchased from Paddock Labs, Minneapolis, Minn.). The wounded liver was replaced in the abdominal cavity, and the peritoneum and skin were closed with appropriate sutures. 100,000 TA3Ha cells were injected into the tail vein, and the animals were examined by autopsy 14 days later. The results are shown in Table 2.

TABLE 2

Effect of topical application of mouse cellular fibronectin on development of local metastatic tumor implants

| | n | Surgical Liver | P |
|---|---|---|---|
| Untreated control mice | 240 | 107 (47%) | |
| Treated with control gel | 29 | 12 (41%) | NS |
| Treated with mouse cFN gel | 35 | 4 (11%) | <.05 |

In the experiment of Example 4, the control gel i.e., suspending agent without fibronectin, did not decrease the percentage of animals with metastatic implants compared to the untreated control mice. When mouse cellular fibronectin was included in the gel, however, and applied topically to the cauterized surface of the liver, there was a statistically significant decrease in the percentage of animals that developed implants at the site of injury in the liver. In some of the individual experiments that were grouped in Table 2, there were no implants in any of the experimental animals. Thus, the percentage of animals with implants is expected to decrease as technique improves.

EXAMPLE 5

Human cellular fibronectin is prepared by a process that is similar to that described in Example 1. Foreskins from newborns were transported in a tissue culture medium, minced, and stirred in trypsin solution in the same manner described in Example 1. The cells were collected by centrifugation and resuspended in MCDB 105 fibroblast culture medium supplemented with 5% fetal bovine serum. The cells were then placed in a closed tissue culture flask for incubation. Because the flasks were closed, the incubator did not require any special type of atmosphere. The medium in the flasks was changed after a week's incubation, and the cells had formed a complete monolayer after 10 days' incubation. The cells were then rinsed, treated with trypsin solution, and then transferred to plastic roller bottles for incubation, as described in Example 1. After five more days of incubation, the cells had completely covered the surface of the roller bottle, and were split again.

After the cells had formed a confluent sheet, the medium was replaced with a fibronectin production medium similar to the fibronectin production medium described in Example 1 but without the essential and the non-essential amino acids. The fibronectin production medium was left on the cells for two days, and then subsequently discarded and replaced with fresh medium which was harvested from the cells every three to four days. It should be noted that because exact timing in harvesting is not critical to this process, the frequency of harvesting may be less or more than the three to four day period shown above. After the harvesting process, fresh fibronectin production medium was placed on the cells.

As mentioned in Example 1, because of the susceptibility of cellular fibronectin to degradation by proteases, the fibronectin was purified from each batch of medium harvested from the cells as soon as possible on the same day it was harvested. Specifically, the medium was filtered through a fiberglass filter and then pumped through an affinity chromatography column containing a bed of gelatin-agarose. The medium was then discarded after passing through the column. The column bed was flushed with equilibration buffer until the absorption at 280 nm had returned to baseline, and then elution buffer was pumped through the column to elute the fibronectin from the affinity bed (see Example 1). A single sharp absorptive peak was collected in fractions 7, 8 and 9 which were pooled and passed through a G-25 column equilibrated with a buffer solution (0.02M sodium chloride, 0.01M sodium phosphate, pH 7.5) to remove the urea. A broad peak was collected in fractions 9 through 11 which was then filtered in a manner similar to that described in Example 1. After lyophilization, the reconstituted freeze-dried product would contain 1 mg/ml of fibronectin, 0.05M phosphate buffer, pH 7.5, 0.1M NaCl. It was then dispensed aseptically into sterile vials to contain 1 mg each of lyophilized fibronectin composition.

The foregoing is for purposes of illustration, rather than limitation of the scope of protection accorded this invention. The latter is to be measured by the following claims, which should be interpreted as broadly as the invention permits.

What is claimed is:

1. A method for producing cellular fibronectin, said method comprising incubating fibronectin-producing cells in a fibronectin production medium comprising:

(a) 1.0–3.5 g/L bicarbonate salt;

(b) 1.0–5.0 g/L glucose;

(c) 10–30 µg/L dexamethasone;

(d) 1–10 g/L hydrolyzed protein; and (e) 5–15 µg/L insulin.

2. The method of claim 1, further comprising an antibiotic.

3. The method of claim 2, wherein the antibiotic is penicillin, at 50,000 to 200,000 units/L, or streptomycin, at 0.05 to 0.2 g/L.

4. The method of claim 1, wherein said hydrolyzed protein comprises lactalbumin hydrolysate.

5. The method of claim 1, wherein said fibronectin production medium comprises 5 to 25 mmol/L HEPES buffer, to give a pH of 6.8 to 7.9.

* * * * *